(12) United States Patent
Lisboa et al.

(10) Patent No.: US 11,759,529 B2
(45) Date of Patent: Sep. 19, 2023

(54) CONTINUOUS COMPLEXATION OF ACTIVE PHARMACEUTICAL INGREDIENTS

(71) Applicant: Hovione Scientia Limited, Cork (IE)

(72) Inventors: Hugo Lisboa, Setúbal (PT); Márcio Temtem, Quinta do Conde (PT); João Vincente, Lisbon (PT); Filipa Santos, Lisbon (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 16/073,469

(22) PCT Filed: Jan. 27, 2017

(86) PCT No.: PCT/GB2017/050210
§ 371 (c)(1),
(2) Date: Jul. 27, 2018

(87) PCT Pub. No.: WO2017/129988
PCT Pub. Date: Aug. 3, 2017

(65) Prior Publication Data
US 2019/0060486 A1    Feb. 28, 2019

(30) Foreign Application Priority Data
Jan. 28, 2016    (PT) ........................................ 109117

(51) Int. Cl.
| | | |
|---|---|---|
| A61K 47/69 | (2017.01) | |
| A61K 9/16 | (2006.01) | |
| A61K 9/14 | (2006.01) | |
| A61K 47/40 | (2006.01) | |
| A61K 31/496 | (2006.01) | |

(52) U.S. Cl.
CPC .......... *A61K 47/6951* (2017.08); *A61K 9/141* (2013.01); *A61K 9/145* (2013.01); *A61K 9/1623* (2013.01); *A61K 9/1694* (2013.01); *A61K 31/496* (2013.01); *A61K 47/40* (2013.01)

(58) Field of Classification Search
CPC .............. A61K 47/6951; A61K 31/496; A61K 9/1694; A61K 9/1623
USPC .......................................................... 514/58
See application file for complete search history.

(56) References Cited

U.S. PATENT DOCUMENTS

| | | |
|---|---|---|
| 5,646,131 A | 7/1997 | Badwan et al. |
| 6,555,139 B2 | 4/2003 | Sharma |
| 6,884,885 B2 | 4/2005 | Qi |
| 2002/0071870 A1* | 6/2002 | Sharma .................. A61K 47/40 424/489 |
| 2002/0086061 A1 | 7/2002 | Sharma |
| 2003/0012774 A1 | 1/2003 | Moldenhauer et al. |
| 2003/0091627 A1 | 5/2003 | Sharma |

FOREIGN PATENT DOCUMENTS

| | | |
|---|---|---|
| JP | 2008169379 A | 7/2008 |
| PT | 109117 | 1/2016 |
| WO | 2008052410 A1 | 5/2008 |
| WO | 2015114320 A1 | 8/2015 |
| WO | 2015154084 A1 | 10/2015 |
| WO | 2017129988 A1 | 8/2017 |

OTHER PUBLICATIONS

Alsarra et al. (Arch Pharm Res vol. 33, No. 7, 1009-1017, 2010).*
Srinivas et al.( Am. J. PharmTech Res. 2014; 4(2), 827-847).*
Shiga et al. (Drying Technology, 19(7), 1385-1395 (2001).*
Wang et al. (Drug Development and Industrial Pharmacy, 32:73-83, 2006).*
Lee et al. (Int. J. Mol. Sci. 2011, 12, 3263-3287).*
Jain et al. (AAPS PharmSciTech, vol. 12, No. 4, Dec. 2011).*
Xu et al. (Shipin Kexue (Beijing, China) (2012), 33(24), 132-136) (Abstract Sent).*
Xu et al. (Shipin Kexue (Beijing, China) (2012), 33(24), 132-136).*
Guedes, Lima, et al., "Ciclodextrinas: como adjuvante tecnológico para melhorar a biodisponibilidade de fármacos," Revista Brasileira de Farmacognosia, 2008, vol. 89, No. 3, pp. 220-225.
Foreign Communication from a related application—International Search Report and Written Opinion of International Application No. PCT/GB2017/050210 dated Apr. 21, 2017, 10 pages.
Foreign Communication from a related application—International Preliminary Report on Patentability of International Application No. PCT/GB2017/050210 dated Feb. 6, 2018, 9 pages.
Kulkarni, Aditya, et al., "Microfluidic Assembly of Cationic-β-Cyclodextrin:Hyaluronic Acid-Adamantane Host:Guest pDNA Nanoparticles," Biomaterials Science, 2013, vol. 1, pp. 1029-1033, The Royal Society of Chemistry.
Liu, Han-Kuei, et al., "Physicochemical Characterizations of Ostholehydroxypropyl-β-cyclodextrin Inclusion Complexes with High-Pressure Homogenization Method," Journal of Food and Drug Analysis, vol. 18, No. 6, 2010, pp. 391-397.

(Continued)

*Primary Examiner* — Layla D Berry (57) ABSTRACT

A complexation process between a cyclodextrin and active pharmaceutical ingredients is disclosed, and comprises a process for preparing a complex of at least one cyclodextrin and at least one active pharmaceutical ingredient comprising the steps of
 a. Preparing a first solution (solution A) comprising at least one cyclodextrin and at least one solvent;
 b. Preparing a second solution (solution B) comprising at least one dissolved, partially dissolved or suspended API;
 c. Mixing said solution A and solution B by means of a microfludization system to produce a solution and/or suspension of at least one of said complex;
 d. Isolating said solution and/or suspension and/or optionally drying it; and
 e. Optionally collecting a powdered form of the complex.
The described process has high throughput with higher yields of complexation in less time than prior art methods. The complexes obtained by the invention are characterized by having enhanced dissolution and/or bioavailability of the active pharmaceutical ingredient in body fluids.

31 Claims, 5 Drawing Sheets

(56) References Cited

OTHER PUBLICATIONS

Foreign Communication from Related Application—Japanese Office Action, Japanese Application No. 2018-539297, dated Nov. 11, 2020, 13 pages.
Imamura, Hitoshi et al., "Recent Trends of Emulsifying Equipment," Journal of Japanese Society of Colour Materials, 2005, pp. 28-33, vol. 78, No. 1.
Srinivas, L. et al., "Preparation and Evaluation of Itraconazole Cyclodextrin Complexes to Enhance their Solubility and Dissolution Parameters," American Journal of Pharmtech Research, 2014, pp. 827-847, vol. 4, No. 2.

* cited by examiner

CONTINUOUS COMPLEXATION OF ACTIVE PHARMACEUTICAL INGREDIENTS

CROSS REFERENCE TO RELATED APPLICATIONS

This application is a filing under 35 U.S.C. 371 of International Application No. PCT/GB2017/050210 filed Jan. 27, 2017, entitled "Continuous Complexation of Active Pharmaceutical Ingredients" which claims priority to Portuguese Patent Application No. 109117 filed Jan. 28, 2016, which applications are incorporated by reference herein in their entirety.

FIELD OF INVENTION

The present invention relates generally to complexes of active pharmaceutical ingredients (API's), particularly to those based on one or more cyclodextrins, and to improved processes for the provision of such complexes.

BACKGROUND OF THE INVENTION

Several active pharmaceutical ingredients have low aqueous solubility which reduces their bioavailability and dissolution in body fluids. Presently, several techniques may be used to overcome this challenge, for example, amorphous solid dispersions, co-crystals, salt formation or cyclodextrin complexation.

Cyclodextrins are cyclic oligosaccharides compounds of 6, 7 or 8 repetitive units with an increasing hydrophobic cavity diameter. They can be designated respectively by alpha, beta or gamma depending on the number of repetitive units. Cyclodextrins can be, for example, prepared by enzymatic conversion of starch. Their external groups are hydrophilic and can be chemically modified, while their internal cavity can be hydrophobic which allows the inclusion of lipophilic molecules, for example, active pharmaceutical ingredients with reduced aqueous solubility.

The inclusion of active pharmaceutical ingredients with reduced aqueous solubility in the internal cyclodextrins cavity, or the formation of a cyclodextrin/active pharmaceutical ingredient complex leads to a high aqueous solubility compound and consequently higher bioavailability in body fluids.

A more detailed description of the advantages and applications of cyclodextrins to overcome the current solubility/bioavailability challenge can be found elsewhere in the literature, namely in the publication "Ciclodextrinas: como adjuvante tecnólogico para melhorar a biodisponiblidade de fármacos", Lima Guedes et al., 2008. This review reports, in general terms, the importance of the use of cyclodextrins as pharmaceutical excipients through the years, it describes in detail cyclodextrins' main chemical derivatives, their mechanism of complexation, as well as their biopharmaceutical and toxicological implications.

The most common method used for the formation of cyclodextrin/active pharmaceutical ingredients complexes is characterized by a process where usually the cyclodextrin is dissolved in water, and then the active pharmaceutical ingredient in its solid form is added to the previous solution. By using, for example, agitation and/or heating, the active pharmaceutical ingredient partially dissolves in water and then forms the complex with the cyclodextrins, allowing the dissolution of additional active pharmaceutical ingredient in solution. To obtain the complex in the powder form, for example, a step of filtration or precipitation followed by drying is required.

The methods presented in the literature have several problems and drawbacks, namely, the high volumes of water usage, low yield due to low quantities of complexation formed, and high process times, requiring 24 h to 172 h to attain the maximum complex concentration, thus, exceeding the stability time of active pharmaceutical ingredients in solution. It is considered that these drawbacks make the industrial use of cyclodextrins less appealing, because of the low throughput. Moreover, the scale up of such processes is typically challenging and cumbersome. In U.S. Pat. No. 6,884,885B2, 2005, the authors claim to solve the first problem by increasing the cyclodextrin concentration but no other indication is given that provides a solution for the remaining problems.

In U.S. Pat. No. 5,646,131 and many other scientific papers, one or more hydrophilic polymers are used to increase the concentration of the complex formed. This makes the process more expensive, and free polymer will be present in the final powder which is considered to be disadvantageous.

In patent applications US2003/0012774A1 and WO2008052410A1, homogenization processes are used and the introduction of energy by homogenization to increase the complexation of the co-enzyme Q10 in γ-cyclodextrin is mentioned. In both patent applications, co-enzyme Q10 is added in the solid state, requiring solubilization and subsequent complexation. The energy used in homogenization serves to solubilize the co-enzyme Q10 into the cyclodextrin solution, namely by decreasing the particle size.

In patent WO2015114320 the authors claim a new scalable process to control the particle size and the particle size distribution of an API and/or excipient by: preparing a suspension in a mixture of solvents where said API and/or excipient is partially soluble in one of the said solvents; reducing the size of the particles present in said suspension using, for example, a homogenization process; ageing the suspension; and stopping the ageing by removing the mixture of solvents. Although the ageing step showed to be key to control the particle size distribution, for the formation of API inclusion complexes this step can be a disadvantage, as said complexes can rapidly dissociate. In general, the formation and dissociation rate of the cyclodextrin/API complexes is similar, and their half-life is only a few thousands of second in solution, meaning that said complexes are continuously being formed and dissociated (Lima Guedes et al., 2008).

In the publication "Physicochemical Characterizations of Osthole-hydroxypropyl-β-cyclodextrin Inclusion Complexes with High-Pressure Homogenization Method", Liu et al., 2010 reported hydroxypropyl-β-cyclodextrin complexation with an active pharmaceutical ingredient, Osthole, using a microfluidization system. In this case a high pressure homogenizer followed by a filtration step and a drying step. This methodology is less efficient than the present invention since it comprises more process steps, mixture before the high pressure homogenizer, 3 cycles in high pressure homogenization and filtration before drying.

In the above-mentioned publications, the active pharmaceutical ingredient had low solubility in the cyclodextrin solution but still the authors tried to dissolve the active pharmaceutical ingredient in such conditions because of the presence of the cyclodextrin. This is considered to be time consuming and an energy waste. Also none of the referred publications provided a continuous process which is an important feature for the economy of the process.

In U.S. Pat. No. 6,555,139B2, US2002/0086061A1, US2003/0091627A1 the authors use a microfluidization system to mill an active pharmaceutical ingredient using a non-solvent, water with a cyclodextrin dissolved. The objective of these publications is not to complex the active pharmaceutical ingredient but to reduce its particle size. In these cases the active pharmaceutical ingredient does not lose its solid form whereas in the present invention, the spontaneous particle size reduction is important for the complexation of the active pharmaceutical ingredient with the cyclodextrin. In these publications cyclodextrins are only used to confer the liquid certain properties and not to complex the API.

In the publication "Microfluidic Assembly of Cationic-β-Cyclodextrin:Hyaluronic Acid-Adamantane Host:Guest pDNA Nanoparticles", Kulkarni et al, 2013, the authors use a microfluidic reactor to mix all components and to precipitate producing solid nanoparticles of complex using flash nanoprecipitation. The present invention considers that obtaining a solution of the complex is advantageous because it can be used in the liquid state for injectable systems and optionally can also be dried to obtain particles suitable for oral delivery.

An objective of the present invention is to provide an improved process for complexation between cyclodextrins and active pharmaceutical ingredients without the disadvantages of the known processes and where it is possible to obtain the desired complexes in less time, with higher complex concentration, with lower solvent quantities, with the possibility of increasing the ratio of active pharmaceutical ingredient/cyclodextrin and where the energy input occurs in a spontaneous way. All these factors contribute to the overall economy of the process.

Unlike the current state-of-the-art, the present invention presents a continuous process of obtaining complexes consisting of a cyclodextrin and active pharmaceutical ingredients dissolved in suitable solvents using a microfluidization system with high levels of mixing and spontaneous heat generation that surprisingly allows complexes to be obtained in less time with high complexation efficiency and that can optionally be followed by spray drying to obtain a solid material.

SUMMARY OF THE INVENTION

The present invention describes a continuous or not continuous process, in particular to obtain cyclodextrin/active pharmaceutical ingredient(s) complexes in reduced time.

According to the present invention, there is provided a process for preparing a complex of at least one cyclodextrin and at least one active pharmaceutical ingredient comprising the steps of:
a. Preparing a first solution (solution A) comprising at least one cyclodextrin and at least one solvent;
b. Preparing a second solution (solution B) comprising at least one dissolved, partially dissolved or suspended API;
c. Mixing said solution A and solution B by means of a microfludization system to produce a solution and/or suspension of at least one of said complex;
d. Isolating said solution and/or suspension and/or optionally drying it; and
e. Optionally collecting a powdered form of the complex.

The present invention thus relates to the increased bioavailability of active pharmaceutical ingredients (API) preferably by the continuous formation of a complex of cyclodextrin and the active pharmaceutical ingredients using a microfluidization system. Alternatively the process can also be combined with spray drying to isolate the complex in powder form. More specifically, the present invention is related to a continuous or dis-continuous complexation process where a first solution of cyclodextrin is combined by microfluidization with a second solution, partial solution, or suspension of an active pharmaceutical ingredient (API) or the solid form of an active pharmaceutical ingredient (API), the first and second solutions (or partial solution, suspension, solid etc.) being either miscible or immiscible. The present invention also concerns the time reduction to obtain such a complex and the combination of a complexation step followed by a spray drying step which can make the present invention a continuous process with high complexation efficiency, where the obtained powder comprising the complex has high drug loading. The present invention thus represents a benefit in terms of reduction of process times.

The process may be a batch process or a continuous process.

Solution A preferably comprises at least one cyclodextrin comprising any substitution group and any cavity size, and/or a polymeric pharmaceutical excipient. The cyclodextrin may, for example, be one or more of α-cyclodextrin, β-cyclodextrin, γ-cyclodextrin, sulfobutylether-beta-cyclodextrin, hydroxypropyl-beta-cyclodextrin, methyl-beta-cyclodextrin and/or maltosyl-beta-cyclodextrin. A particularly preferred cyclodextrin is sulfobutylether-beta-cyclodextrin.

Solution A preferably comprises at least one of the following solvents: water, ethanol, methanol, isopropanol, dichloromethane acetone, methyl ethyl ketone, tetrahydrofuran, di-methyl sulfoxyde, di-methyl formaldehyde, or di-methyl acetamide.

The concentration of cyclodextrin in solution A preferably ranges from 1 to 50% (w/w).

If desired, a polymeric pharmaceutical excipient may be present in solution A, for example at a concentration of from 1 to 20% (w/w).

The pH of solution A typically ranges from 1 to 14, and a preferred pH is 6 to 8.

In the process of the invention, solution A is preferably prepared using a jacketed reactor with agitation, by adding at least one solvent to the reactor and at least one cyclodextrin to the same reactor and/or at least one polymeric pharmaceutical excipient to the same reactor, typically followed by pH adjustment. The order of the addition of the above components is not restricted and can be any way round.

Solution B preferably comprises at least one API dissolved in one or more solvents, partially dissolved in one or more solvents, or in suspension in one or more solvents. Preferably, the API or its pharmaceutically acceptable derivative has at least one functional group selected from: thiother, alcohol, thiol, aldehyde, ketone, thioketone, nitrate ester, phosphate ester, thiophosphate ester, ester, thioester, sulfate ester, carboxylic acid, phosphonic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heteocyclic ring, furan, epoxide, peroxide, hydroxamic acid, imidazole, and pyridine.

Examples of preferred APIs include, but are not limited to, poorly soluble active compounds. Examples of poorly soluble compounds include, but are not limited to: antifungal agents like itraconazole or a related drug, such as fluoconazole, terconazole, ketoconazole and saperconazole; anti-infective drugs, such as griseofulvin and related compounds (e.g. griseoverdin); anti malaria drugs (e.g. Atovaquone); protein kinase inhibitors such as Afatinib, Axitinib, Bosutinib, Cetuximab, Crizotinib, Dasatinib, Erlotinib, Fostamatinib, Gefitinib, Ibrutinib, Imatinib, Zemurasenib, Lapatinib, Lenvatinib, Mubritinib or Nilotinib; immune system modulators (e.g. cyclosporine); cardiovascular drugs (e.g. digoxin and spironolactone); ibuprofen; sterols or steroids; drugs from the group comprising danazol, acyclovir, dapsone, indinavir, nifedipine, nitrofurantion, phentytoin, ritonavir, saquinavir, sulfamethoxazole, valproic acid, trimethoprin, acetazolamide, azathioprine, iopanoic acid, nalidixic acid, nevirapine, praziquantel, rifampicin, albendazole, amitrptyline, artemether, lumefantrine, chloropromazine, ciprofloxacin, clofazimine, efavirenz, iopinavir, folic acid, glibenclamide, haloperidol, ivermectin, mebendazole, niclosamide, pyrantel, pyrimethamine, retinol vitamin, sulfadiazine, sulfasalazine, triclabendazole, and cinnarizine.

Solution B preferably comprises at least one of the following solvents: water, ethanol, methanol, isopropanol, dichloromethane, acetone, methyl ethyl ketone, tetrahydrofuran, di-methyl sulfoxyde, di-methyl formaldehyde, or di-methyl acetamide.

In the invention, the one or more solvents in solution B can be the same or different from those solvents in Solution A, and if different said solvents can be miscible or immiscible with each other.

The concentration of API in solution B preferably ranges from 0.01 to 100% (w/w).

Solution B is typically prepared using a jacketed reactor with agitation, by adding at least one solvent to the reactor and at least one API. The order of addition of the components is not restricted and can be any way around.

In one aspect, if desired, a solid API may be fed continuously, for example, by a positive displacement equipment, such as a screw-based feeding system or a pneumatic system.

In one preferred aspect, the solid API is fed continuously, preferably using a hopper.

The microfludization preferably occurs in a system comprising at least one intensifier pump that can mix and displace a liquid mixed with another miscible or immiscible liquid, or alternatively a liquid mixed with a solid compound, into at least one micro-channel or micro-reactor. Two or more micro-channels or micro-reactors may be used if desired.

Preferably, the micro-channel or micro-reactor is a continuous flow reactor, suitably with a lateral dimension of equal to or below 1000 microns. The lateral dimension may be equal to or below 200 microns.

The hydrodynamic pressure of the process preferably ranges from 1 bar to 1500 bar, and may suitably range from 250 to 1000 bar.

In a preferred aspect of the invention, the feed flow ratio of solution A to solution B or solid API ranges from about 0.1 to about 10 kg/kg. The feed flow ratio of solution A and the amount of API added can range from 0.01 to 10 kg/kg.

The process temperature can be any suitable temperature, bearing in mind the components involved, and it suitably ranges from 0° C. to 90° C.

Isolation of the complex from the complex solution and/or suspension may be by any means, but preferably comprises one or more drying techniques. One particularly suitable drying technique comprises spray drying.

In the process of the invention, isolation of the complex from the complex solution and/or suspension may be a batch process or continuous process.

In a preferred aspect, the complex is isolated in powdered form.

It will be appreciated that the complexes produced by the method of the invention may be used in medicine, for example as part of a pharmaceutical composition. The invention thus provides this use, or alternatively a process characterized in that the obtained complex in solution and/or suspension or powdered form is used for pharmaceutical purposes.

In a preferred aspect, the invention provides a process for preparing a complex of at least one cyclodextrin and at least one active pharmaceutical ingredient comprising the steps of
 a) Preparation of Solution A with at least one cyclodextrin in one or more solvents;
 b) Preparation of Solution B with at least one dissolved or suspended API. The solvent can be the same or different than Solution A, and if different can be miscible or immiscible. Alternatively the active pharmaceutical ingredient(s) are added in the solid state by means of a positive displacement equipment, preferably a hopper and a screw feed;
 c) Continuous mixing of the solutions A and B or API in solid state using a microfluidization system that comprises an intensifier pump that draws and mix all components to the high pressure chamber creating cavitation and then displace the mixture into at least one micro-channel, forming a complex solution;
 d) Optionally separate the complex from the solution continuously or not continuously by any method of separation such as crystallization, filtration or drying; preferably spray drying.

The present invention presents lower complexation times for the formation of the complex between the cyclodextrin and the at least one active pharmaceutical ingredient allowing to use the present invention for continuous manufacture of cyclodextrin complexes because of high levels of mixing and spontaneous heat generation that surprisingly create a high concentration of a desired complex. When combined, for example, with spray drying, it is possible to obtain a powder comprising the same complex.

The present invention also presents a method to obtain powder with higher concentration of the active pharmaceutical ingredient complexed with the cyclodextrin in less time than other known processes.

Preferentially, the present invention allows the continuous production of cyclodextrin/active pharmaceutical ingredient complex and its continuous isolation using spray drying.

The present invention comprises a microfluidization system. The microfluidization system typically consists of an intensifier pump that can mix and displace a liquid mixed with another miscible or immiscible liquid, or alternatively a liquid mixed with a solid compound, into a combination of micro-channels. A micro-channel is typically a continuous flow reactor with lateral dimensions less of 1000 μm.

Figure 1:
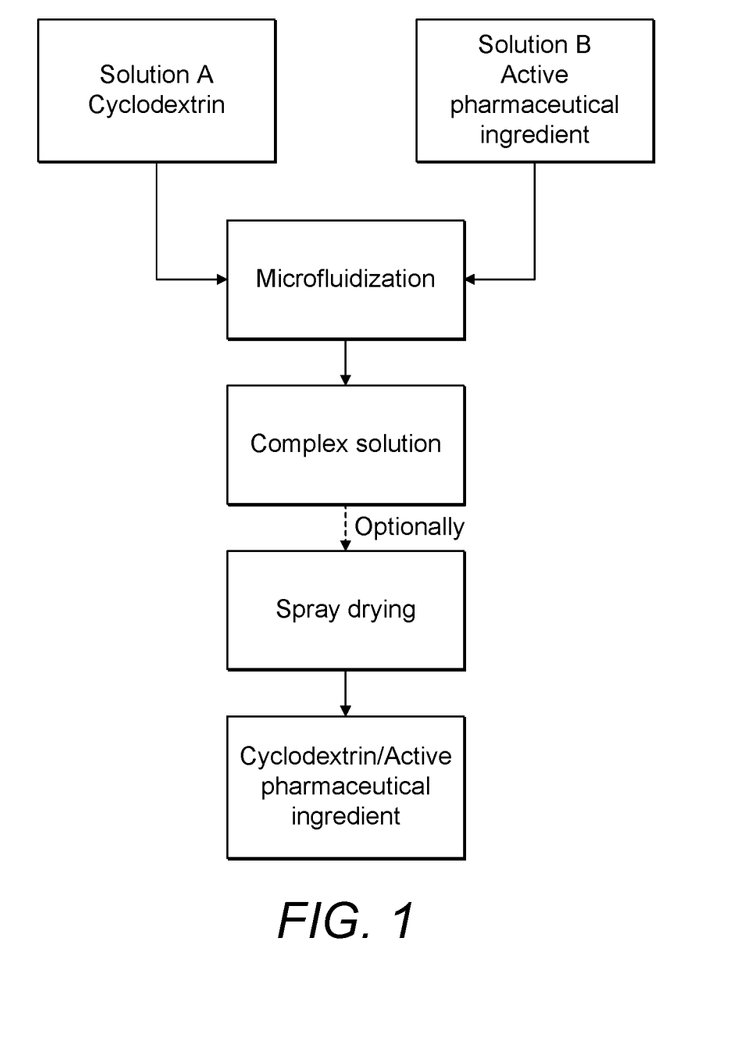
FIG. 1 shows a schematic flowchart of the present invention process.
Figure 2:
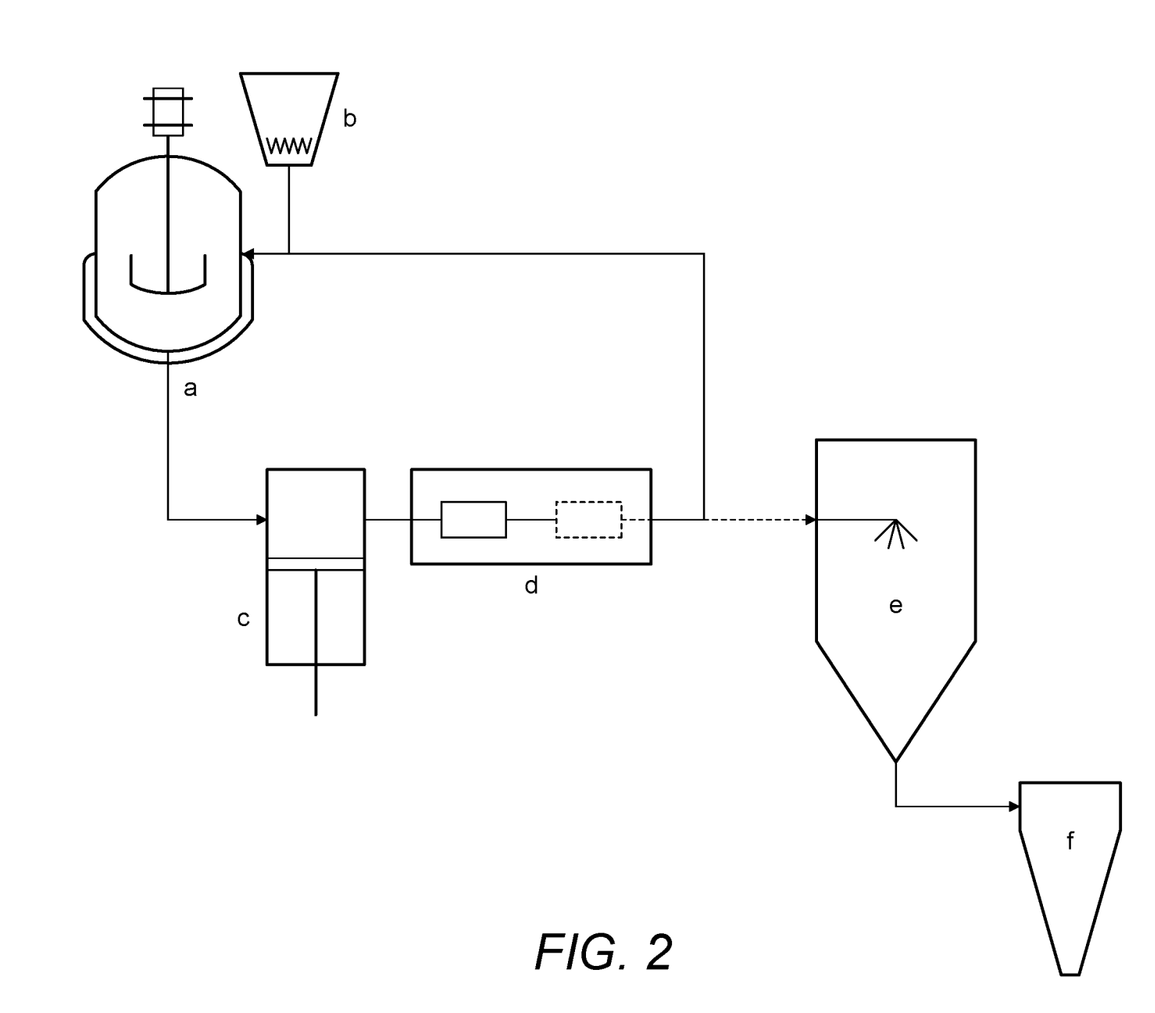
FIG. 2 shows a schematic drawing of setup A, where a) is a mixing reactor, b) is a positive displacement equipment, c) is an intensifier pump, d) a combination of at least one micro-channel, e) is a drying chamber and f) is a cyclone.

Preferentially, the present invention uses two different setups:
 Setup A comprising:
 a) A reactor to prepare Solution A;
 b) A positive displacement equipment such as an hopper and screw feed to displace a solid API into reactor a);
 c) An intensifier pump;
 d) A combination of at least one micro-channel.

Figure 3:
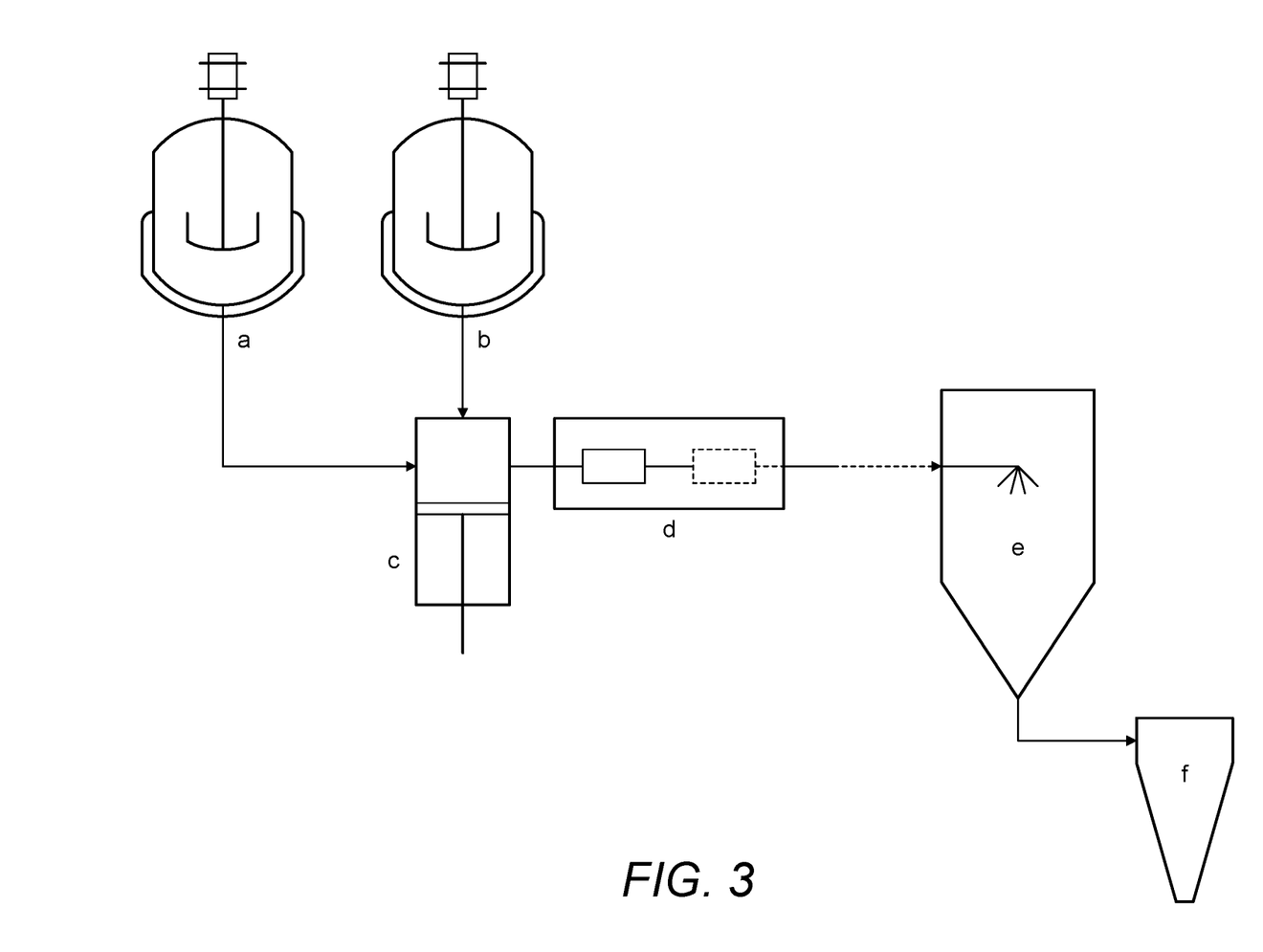
FIG. 3 shows a schematic drawing of setup B, where a) is a mixing reactor, b) is a second mixing reactor, c) is an intensifier pump, d) a combination of at least one micro-channel, e) is a drying chamber and f) is a cyclone.

Optionally a spray dryer and a cyclone to collect the powdered complex;

Setup B
a) A reactor to prepare Solution A;
b) A reactor to prepare Solution B;
c) An intensifier pump;
d) A combination of at least one micro-channel.

Optionally, a spray dryer and a cyclone to collect the powdered complex.

DETAILED DESCRIPTION OF THE INVENTION

The present invention presents a continuous or not continuous process for the complexation of a cyclodextrin and at least one active pharmaceutical ingredient optionally followed by a drying step. The drying step can, for example, be a spray drying process, but other suitable drying processes may be used.

More specifically, the present invention presents a continuous or not continuous (i.e. dis-continuous) process for the complexation of a cyclodextrin and at least one active pharmaceutical ingredient by mixing a solution A comprising at least one dissolved cyclodextrin and solution B comprising at least one dissolved or suspended API or alternatively the solid API fed by a positive displacement equipment, preferably a hopper equipped with a screw feed, forming stream B. Then using an intensifier pump, draw stream A and stream B and mix them into the pump high pressure chamber causing cavitation and then displace the mixed streams into at least one micro-channel, that creates high shear mixing, milling the API by cavitation, spontaneously produces heat due to friction and surprisingly produces a complex solution comprising high concentration of the complex. If combined with a spray drying step, the obtained complex solution is continuously or not continuously dried producing the complex of cyclodextrin and active pharmaceutical ingredient in the powder form.

Solution A comprises a solution with one or more solvents, that are preferably chosen from, water, ethanol, methanol, isopropanol, dichloromethane, acetone, Methyl Ethyl Ketone, TetraHydroFuran, Di-methyl Sulfoxyde, Di-methyl Formaldehyde, or Di-methyl Acetamide. The solution A also comprises one or more dissolved cyclodextrins or substituted cyclodextrins. Any cyclodextrin or substituted cyclodextrin may be used, and preferred compounds include, for example, α-cyclodextrin, β-cyclodextrin, γ-cyclodextrin, sulfobutylether-beta-cyclodextrin, hydroxypropyl-beta-cyclodextrin, methyl-beta-cyclodextrin and/or maltosyl-beta-cyclodextrin. Any suitable pharmaceutical excipient(s) can also be added to solution A with, for example, a concentration of from 1% (w/w) to 20% (w/w). The concentration of the one or more cyclodextrins is preferably from 1% (w/w) to 50% (w/w). Solution A has a pH value ranging from 1 to 14, preferably of from 6 to 8. Solution A can be prepared, for example, using a jacketed reactor with agitation, by adding solvent to the reactor and by adding cyclodextrin(s) to the same reactor, followed by the pH adjustment. The order of addition is nor restricted and can be done either way around.

Solution B comprises a solution or suspension using one or more solvents, which are preferably chosen from, water, ethanol, methanol, isopropanol, dichloromethane, acetone, Methyl Ethyl Ketone, TetraHydroFuran, Di-methyl Sulfoxyde, Di-methyl Formaldehyde, or Di-methyl Acetamide. Solution B also comprises at least one active pharmaceutical ingredient (API) which may be dissolved, partially dissolved or in suspension in the solvent. The API is preferably present at a concentration ranging from 0.01% (w/w) to 100% (w/w). Alternatively, active pharmaceutical ingredients in their solid form can be used. Solution B may, for example, be prepared using a jacketed reactor with agitation where, the solvent or solvents and the at least one Active pharmaceutical ingredient are added to the reactor. The order of addition is not restricted and can be done either way around.

Alternatively, the at least one API in the solid form can be directly added to the mixture. Preferably, the API in solid form is added by a positive displacement equipment, preferably comprising a hopper or a screw feed or by pneumatic means.

Accordingly to the present invention, an optimum feed flow ratio between the Solution A and Solution B exists. Therefore, for example, a feed flow of Solution A to the microfluidization system can range from 0.1 to 10 times the Solution B feed flow to the microfluidization system. Ratios of 0.5 to 5, or 0.5 to 3, or 1 to 3 may also be used (as per above definition).

Alternatively, in the present invention, an optimum ratio between the feed flow rate of solution A and the amount of solid API added exists. Therefore, for example, a feed flow of Solution A to the microfluidics equipment can range from 0.01 to 10 times the amount of solid active pharmaceutical ingredient added. Ratios of 0.1 to 10, or 0.1 to 5, or 0.5 to 3, or 1 to 3 may also be used (as per above definition).

According to the present invention, the mixture of all compounds and complexation is performed in a microfluidization system. "Microfluidization" is a term understood by those skilled in this field. The term "microreaction" refers to a technology that involves physical and/or chemical reactions within microreactors, micromixers, microchannels or any other component comprised within the microfluidic field. The term "microfluidization" encompasses continuous fluid processing through these microchannels, involving high shear, cavitation and uniform mixing in the meso- and micromixing range. The microfluidization system comprises, for example, an intensifier pump that draws stream A and solution B or the at least one API in the solid form, continuously or not (i.e. dis-continuously), into the pump chamber and then pushes the mixture of streams through the at least one micro-channel, producing high pressure, spontaneous heat generation, friction, cavitation, high shear mixing at high Reynolds numbers, and milling if the API is in the solid state. We have found that, surprisingly, a high concentration of complex is obtained at the end of the pressurized pathway. The formation of the complex comprises the dissolution of the at least one API and consequently inclusion in the cavity of the at least one cyclodextrin. The number of micro-channels is not limited and can be at least one, but preferably rangesng from 1 to 10. The lateral dimensions of the micro-channels are lower than about 1000 μm, and are preferably equal to or lower than about 200 μm. The pump creates pressures ranging from 1 to 1500 Bar (can we give some preferred sub-ranges?), and the mixed liquid temperature is spontaneously increased which represents an increase in efficiency as less energy is spent drying the mixed liquid. At the end of the process, a solution with a high concentration of the cyclodextrin/active pharmaceutical ingredient complex is obtained in much less time than reported previously.

The obtained solution can, if desired, be continuously or not continuously fed into a spray dryer. For example, the spray dryer may be equipped with a nozzle that atomizes the complex solution into droplets and a passing drying gas with a flowrate of 1 to 2000 Kg/h, and using temperatures ranging from 0 to 200° C., to dry the complex solution droplets into solid particles that are collected in a cyclone. At the end of the spray drying operation, a powder with a high content of cyclodextrin/active pharmaceutical ingredient complex is obtained.

The present invention can be a continuous process or a non-continuous process. For example, in a non-continuous embodiment, setup A, the solution A and solution B or solid API may be pre-mixed in a reactor, microfluidized and then recycled back to the same reactor producing the complex solution. Optionally, the said complex solution from this embodiment is dried, for example using spray drying or freeze drying.

In a continuous embodiment, for example setup B, the present invention discloses a method where solution A and solution B or solid API are microfluidized producing the complex solution. Optionally, the said complex solution is continuously fed to a continuous drier, for example a spray dryer.

The present invention has a high throughput due to the increased amount of solid complex obtained per process time. This is achieved due to the combination of three major effects: reduced dissolution times of components in solution A and solution B; reduced complexation times due to increased levels of mixing, milling and spontaneous temperature increasing the complex concentration in the complex solution; and finally by optionally continuously feeding said complex solution into the spray drying to obtain the solid complex.

EXAMPLES

Example 1

Figure 4:
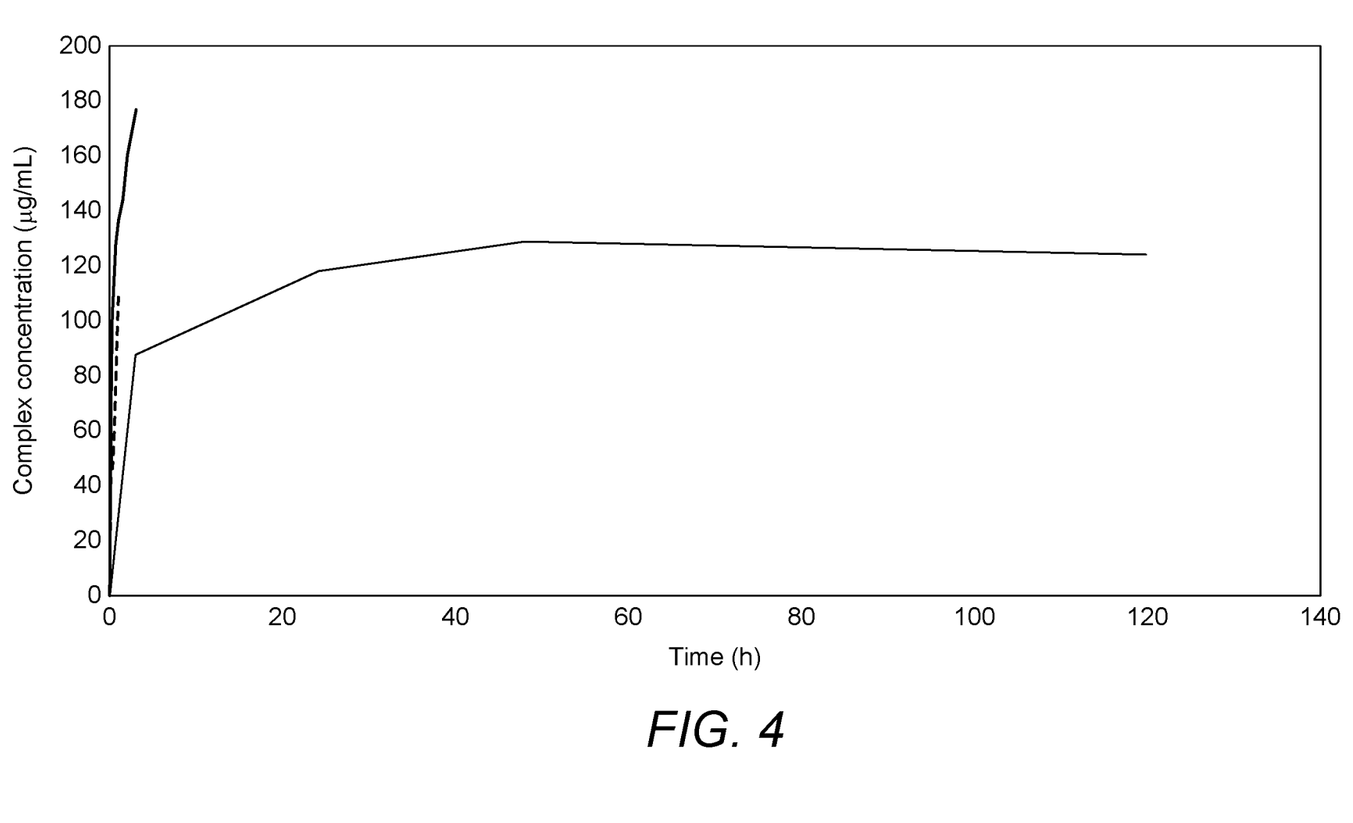
FIG. 4 shows a representation of the concentration of complex formed vs time. Dotted line represents the example 1 method. The dashed line represents example 2 method. The solid line represents the example 3 method.
Figure 5:
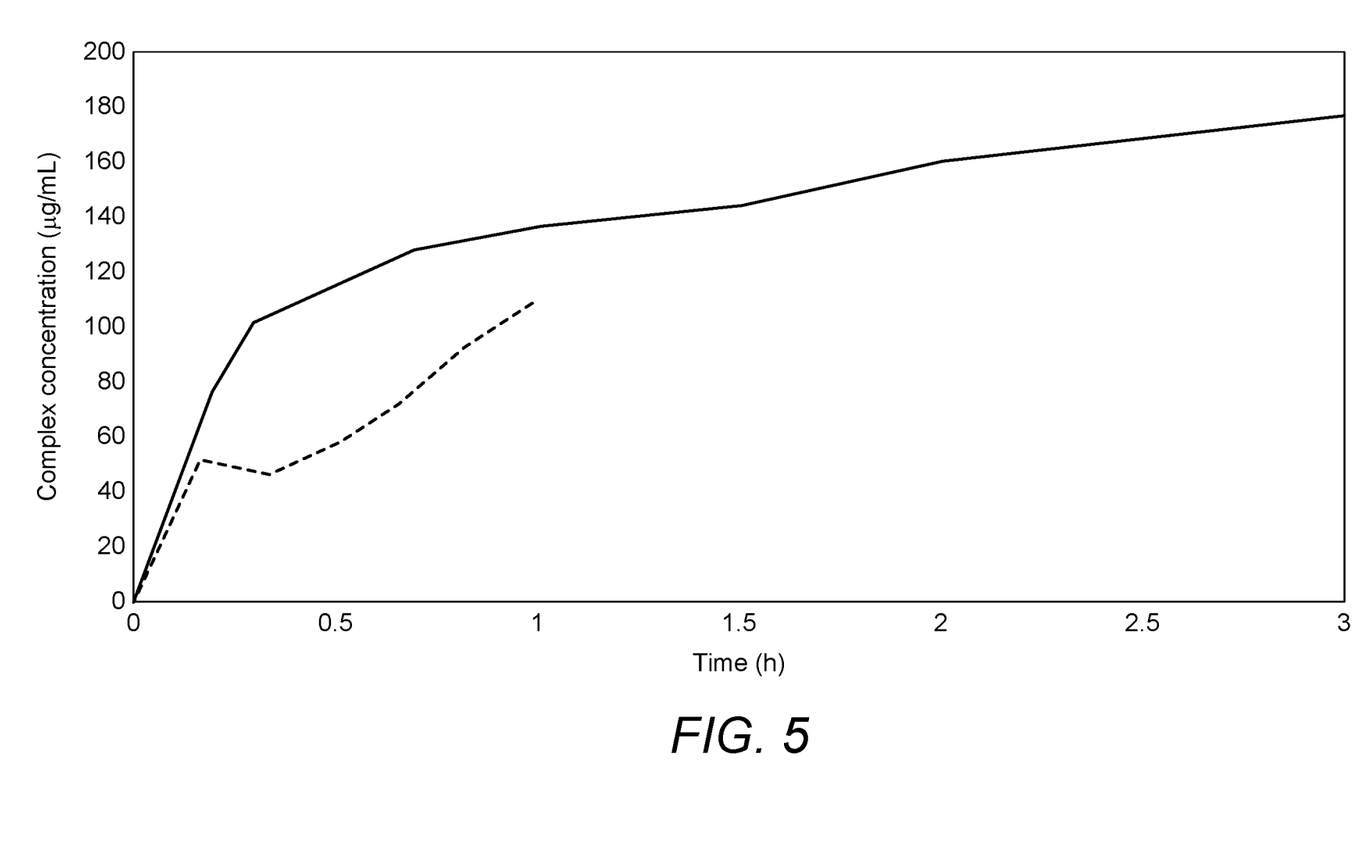
FIG. 5 corresponds to a "zoom in" of the first 3 hours of FIG. 4 for example 2 (dashed line) and example 3 (solid line).

60 grams of water were added to a reactor with agitation. To this reactor 40 grams of sulfobutylether-β-Cyclodextrin were added. The suspension was agitated continuously until a clear solution was formed. Then 1 gram of an active pharmaceutical ingredient (in this case Itraconazole was used as the model drug) was added to the said solution and a timer was immediately set. The formed suspension was agitated continuously at 25° C. Each day a 2 g of said suspension was filtered and analyzed by HPLC to determine complex concentration. Results are shown in FIG. 4 (dotted line).

Example 2

60 grams of water were added to a reactor with agitation. To this reactor 40 grams of sulfobutylether-β-Cyclodextrin were added. The suspension was agitated continuously until a clear solution was formed. Using setup A, 10 gram of an active pharmaceutical ingredient (itraconazole) was added to the said solution and a timer was immediately set. The formed suspension was fed to an intensifier pump at a pressure of 550 bar at room temperature for 1 hour. At each 10 min, a 2 g sample from the suspension was filtered and analyzed by HPLC to determine complex concentration. After 1 h the solution was spray dried to produce a powdered material. Results are shown in FIG. 4 (dashed line).

Example 3

60 grams of water were added to a reactor with agitation. To this reactor 400 grams of sulfobutylether-β-Cyclodextrin were added. The suspension was agitated continuously until a clear solution was formed. Using setup A, 10 gram of an active pharmaceutical ingredient (itraconazole) was added to the said solution and a timer was immediately set. The formed suspension was fed to an intensifier pump at a pressure of 550 bar and room temperature for 3 hours. At each 10 min, a 2 g sample from the suspension was filtered and analyzed by HPLC to determine complex concentration. After 3 h the solution was spray dried to produce a powdered material. Results are shown in FIG. 4 (solid line).

Example 4

60 grams of water were added to a reactor with agitation. To this reactor 40 grams of sulfobutylether-β-Cyclodextrin were added. In another reactor 90 grams of dichloromethane were added. To this reactor 10 grams of an active pharmaceutical ingredient (itraconazole) was added. Both solutions were agitated continuously until a clear solution was formed. Using setup B, both solutions were fed to an intensifier pump with a feed flow ratio of 10 kg/kg of solution A per solution B, and a pressure of 1000 bar at a temperature of 50° C. was produced. The obtained solution was sampled to determine the complex concentration. The solution was then spray dried to form a powdered material.

The invention claimed is:
1. A process for preparing a complex comprising at least one cyclodextrin and at least one active pharmaceutical ingredient (API) comprising the steps of:
   a. Preparing a first solution (solution A) comprising the at least one cyclodextrin selected from the group consisting of: α-cyclodextrin, β-cyclodextrin, γ-cyclodextrin, sulfobutylether-beta-cyclodextrin, hydroxypropyl-beta -cyclodextrin, methyl-beta-cyclodextrin and maltosyl-beta-cyclodextrin, and at least one solvent;
   b. Preparing a second solution, partial solution or suspension (solution B), comprising the at least one API;
   c. Feeding said solution A and said solution B to a microfluidization system, wherein the feed flow ratio of solution A to the microfluidization system to solution B ranges from 0.1 to 10 kg/kg and the feed flow ratio of solution A to the microfluidization system and the amount of solid API added ranges from 0.01 to 10 kg/kg;
   d. Mixing said solution A and said solution B by a microfluidization system to produce a third solution (solution C) of at least one of said complex such that the at least one API is included in an internal cyclodextrin cavity;
   e. Isolating said solution C and/or optionally drying the solution C; and f. Optionally collecting a powdered form of the complex comprising the at least one cyclodextrin and the at least one active pharmaceutical ingredient (API).

2. The process according to claim 1, wherein the process is a batch process or a continuous process.

3. The process according to claim 1, wherein solution A comprises at least one cyclodextrin comprising any substitution group and any cavity size, and/or a polymeric pharmaceutical excipient.

4. The process according to claim 1, wherein the cyclodextrin is sulfobutylether-beta-cyclodextrin.

5. The process according to claim 1, wherein solution A comprises at least one of the following solvents: water, ethanol, methanol, isopropanol, dichloromethane acetone, methyl ethyl ketone, tetrahydrofuran, di-methyl sulfoxyde, di-methyl formaldehyde, or di-methyl acetamide.

6. The process according to claim 1, wherein the concentration of cyclodextrin in solution A ranges from 1 to 50% (w/w).

7. The process according to claim 1, wherein a polymeric pharmaceutical excipient is present in solution A at a concentration of from 1 to 20% (w/w).

8. The process according to claim 1, wherein the pH of solution A ranges from 1 to 14.

9. The process according to claim 8, wherein the pH is 5 to 7.

10. The process according to claim 1, wherein solution A is prepared using a jacketed reactor with agitation, by adding the at least one solvent to the reactor and the at least one cyclodextrin to the reactor and/or at least one polymeric pharmaceutical excipient to the reactor, followed by pH adjustment.

11. The process according to claim 10, wherein the order of addition of the components of solution A is not restricted.

12. The process according to claim 1, wherein solution B comprises at least one API dissolved in one or more solvents.

13. The process according to claim 12, wherein the API or its pharmaceutically acceptable derivative has at least one functional group selected from:
   thiother, alcohol, thiol, aldehyde, ketone, thioketone, nitrate ester, phosphate ester, thiophosphate ester, ester, thioester, sulfate ester, carboxylic acid, phosphonic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heteocyclic ring, furan, epoxide, peroxide, hydroxamic acid, imidazole, and pyridine.

14. The process according to claim 1, wherein solution B comprises at least one of the following solvents: water, ethanol, methanol, isopropanol, dichloromethane, acetone, methyl ethyl ketone, tetrahydrofuran, di-methyl sulfoxyde, di-methyl formaldehyde, or di-methyl acetamide.

15. The process according to claim 1, wherein solution B further comprises one or more solvents that can be the same or different from the at least one solvent in Solution A, and if different said solvents can be miscible or immiscible with each other.

16. The process according to claim 1, wherein the concentration of API in solution B ranges from 0.01 to 100% (w/w).

17. The process according to claim 12, wherein solution B is prepared using a jacketed reactor with agitation, by adding at least one solvent to the reactor and at least one API.

18. The process according to claim 17, wherein the order of addition of the components of solution B is not restricted.

19. The process according to claim 17, wherein a solid API is fed continuously by a positive displacement equipment comprising a screw-based feeding system or a pneumatic system.

20. The process according to claim 19, wherein the solid API is fed continuously using a hopper.

21. The process according to claim 1, wherein the microfluidization system comprises at least one intensifier pump and at least one micro-channel or micro-reactor, wherein the intensifier pump can mix and displace a liquid mixed with another miscible or immiscible liquid, or alternatively a liquid mixed with a solid compound, into the at least one micro-channel or micro-reactor.

22. The process according to claim 21, wherein the at least one micro-channel or micro-reactor is a continuous flow reactor with a lateral dimension of equal to or below 1000 microns.

23. The process according to claim 22, wherein the lateral dimension is equal to or below 200 microns.

24. The process according to claim 22, wherein the hydrodynamic pressure of the process ranges from 1 bar to 1500 bar.

25. The process according to claim 24, wherein the hydrodynamic pressure of the process ranges from 250 to 1000 bar.

26. The process according to claim 1, wherein the process temperature ranges from 0° C. to 90° C.

27. The process according to claim 1, further comprising isolating the complex from the solution C, wherein isolation of the complex from the solution C comprises one or more drying techniques.

28. The process according to claim 27, wherein the drying technique comprises spray drying.

29. The process according to claim 27, wherein isolation of the complex from the solution C is a batch process or continuous process.

30. The process according to claim 27, wherein the complex is isolated in powdered form.

31. The process according to claim 1, characterized in that the complex in solution C or powdered form is used for pharmaceutical purposes.

* * * * *